US009126031B2

(12) United States Patent
Tekmen et al.

(10) Patent No.: US 9,126,031 B2
(45) Date of Patent: Sep. 8, 2015

(54) MEDICAL ELECTRICAL LEAD WITH CONDUCTIVE SLEEVE HEAD (75) Inventors: Mohac Tekmen, White Bear Lake, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 284 days.

(21) Appl. No.: 13/097,187

(22) Filed: Apr. 29, 2011

(65) Prior Publication Data

US 2011/0270369 A1    Nov. 3, 2011

Related U.S. Application Data (60) Provisional application No. 61/329,793, filed on Apr. 30, 2010.

(51) Int. Cl.
*A61N 1/00* (2006.01)
*A61N 1/05* (2006.01)
*A61N 1/08* (2006.01)

(52) U.S. Cl.
CPC .............. *A61N 1/0573* (2013.01); *A61N 1/056* (2013.01); *A61N 2001/086* (2013.01)

(58) Field of Classification Search
CPC ..... A61N 1/086; A61N 1/056; A61N 1/0573; A61N 2001/086; A61N 1/05; A61N 1/0565
USPC .................................................. 607/115, 116
See application file for complete search history.

(56) References Cited

U.S. PATENT DOCUMENTS

| | | |
|---|---|---|
| 4,917,104 A | 4/1990 | Rebell |
| 5,445,859 A | 8/1995 | Lindegren et al. |
| 5,824,030 A | 10/1998 | Yang et al. |
| 6,944,489 B2 | 9/2005 | Zeijlemaker et al. |
| 6,985,775 B2 | 1/2006 | Reinke et al. |
| 7,174,219 B2 | 2/2007 | Wahlstrand et al. |

(Continued)

FOREIGN PATENT DOCUMENTS

| | | |
|---|---|---|
| CN | 1269708 A | 8/2006 |
| CN | 1907514 A | 2/2007 |

(Continued)

OTHER PUBLICATIONS (PCT/US2011/034480) PCT Notification of Transmittal of the International Search Report and the Written Opinion of the International Searching Authority, Mailed Aug. 30, 2011, 10 pages.

(Continued)

*Primary Examiner* — Niketa Patel
*Assistant Examiner* — William Levicky
(74) *Attorney, Agent, or Firm* — Michael J. Ostrom (57) ABSTRACT This disclosure provides a medical lead assembly that includes a lead body having a proximal end configured to couple to an implantable medical device and a distal end. The lead assembly further includes an electrode assembly located at the distal end of the lead body, the electrode assembly including a tip electrode, a conductive electrode shaft that is electrically coupled to the tip electrode and an energy dissipating structure that is coupled to at least a portion of the conductive electrode shaft at high frequencies to redirect at least a portion of the current induced in the lead by a high frequency signal from the tip electrode to the energy dissipating structure.

12 Claims, 9 Drawing Sheets

(56) References Cited

U.S. PATENT DOCUMENTS

| | | | |
|---|---|---|---|
| 7,289,856 B1 | 10/2007 | Karicherla | |
| 7,363,090 B2* | 4/2008 | Halperin et al. | 607/116 |
| 7,689,288 B2 | 3/2010 | Stevenson et al. | |
| 7,751,903 B2 | 7/2010 | Stevenson et al. | |
| 7,877,150 B2* | 1/2011 | Hoegh et al. | 607/119 |
| 2002/0128691 A1 | 9/2002 | Connelly | |
| 2003/0083723 A1 | 5/2003 | Wilkinson et al. | |
| 2003/0144718 A1* | 7/2003 | Zeijlemaker | 607/122 |
| 2003/0216800 A1 | 11/2003 | Ebert et al. | |
| 2004/0064024 A1 | 4/2004 | Sommer | |
| 2005/0070972 A1 | 3/2005 | Wahlstrand et al. | |
| 2005/0090886 A1 | 4/2005 | MacDonald et al. | |
| 2005/0159661 A1 | 7/2005 | Connelly et al. | |
| 2005/0222658 A1* | 10/2005 | Hoegh et al. | 607/116 |
| 2006/0200218 A1 | 9/2006 | Wahlstrand | |
| 2006/0247747 A1 | 11/2006 | Olsen et al. | |
| 2006/0247748 A1 | 11/2006 | Wahlstrand et al. | |
| 2006/0259088 A1 | 11/2006 | Pastore et al. | |
| 2007/0093142 A1 | 4/2007 | MacDonald et al. | |
| 2007/0208383 A1 | 9/2007 | Williams | |
| 2007/0244535 A1 | 10/2007 | Inman et al. | |
| 2007/0299490 A1 | 12/2007 | Yang et al. | |
| 2008/0009905 A1 | 1/2008 | Zeijlemaker | |
| 2008/0116997 A1 | 5/2008 | Dabney et al. | |
| 2008/0132985 A1 | 6/2008 | Wedan et al. | |
| 2008/0147154 A1 | 6/2008 | Gray et al. | |
| 2008/0154346 A1 | 6/2008 | Smith et al. | |
| 2008/0154348 A1 | 6/2008 | Atalar et al. | |
| 2008/0221568 A1 | 9/2008 | Stone | |
| 2008/0269830 A1* | 10/2008 | Marshall | 607/37 |
| 2008/0269855 A1 | 10/2008 | Marshall | |
| 2008/0281390 A1* | 11/2008 | Marshall | 607/116 |
| 2009/0149920 A1 | 6/2009 | Li et al. | |
| 2009/0149934 A1 | 6/2009 | Ameri et al. | |
| 2009/0198314 A1 | 8/2009 | Foster et al. | |
| 2009/0240296 A1 | 9/2009 | Zeijlemaker et al. | |
| 2010/0023000 A1* | 1/2010 | Stevenson et al. | 606/33 |
| 2010/0217262 A1 | 8/2010 | Stevenson et al. | |
| 2010/0312294 A1 | 12/2010 | Martinez et al. | |
| 2011/0034979 A1 | 2/2011 | Min et al. | |
| 2011/0040343 A1 | 2/2011 | Johnson et al. | |
| 2011/0071604 A1 | 3/2011 | Wahlstrand et al. | |
| 2011/0118813 A1 | 5/2011 | Yang et al. | |

FOREIGN PATENT DOCUMENTS

| | | |
|---|---|---|
| WO | 03037424 A2 | 5/2003 |
| WO | 2008036865 A2 | 3/2008 |
| WO | 2008095059 A1 | 8/2008 |
| WO | 2009134901 A1 | 11/2009 |
| WO | 2010008833 A1 | 1/2010 |

OTHER PUBLICATIONS

Office Action from U.S. Appl. No. 12/915,631, dated May 24, 20013, 26 pages.

Response to Office Action from U.S. Appl. No. 12/915,631, submitted Aug. 26, 2013, 11 pages.

Final Office Action from U.S. Appl. No. 12/915,631, dated Mar. 17, 2014, 13 pages.

Response to Final Office Action from U.S. Appl. No. 12/915,631, submitted May 19, 2014, 4 pages.

Advisory Action from U.S. Appl. No. 12/915,631, dated Jun. 26, 2014, 3 pages.

Pre-Appeal Brief Request and Notice of Appeal from U.S. Appl. No. 12/915,631, submitted on Jul. 17, 2014.

* cited by examiner

MEDICAL ELECTRICAL LEAD WITH CONDUCTIVE SLEEVE HEAD

This application claims the benefit of U.S. Provisional Application No. 61/329,793, filed on Apr. 30, 2010, the content of which is incorporated herein by reference in its entirety.

TECHNICAL FIELD

The present disclosure relates to implantable medical devices (IMDs) and, more particularly, to a medical electrical lead with a conductive sleeve head for redirecting current induced from high frequency signals.

BACKGROUND

In the medical field, implantable leads are used with a wide variety of medical devices. For example, implantable leads are commonly used to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads are also used for sensing purposes, or for both sensing and stimulation purposes. Implantable leads are also used in neurological devices, muscular stimulation therapy, and devices that sense chemical conditions in a patient's blood, gastric system stimulators.

Occasionally, patients that have implantable leads may benefit from a magnet resonance image being taken of a particular area of his or her body. Magnetic resonance imaging (MRI) techniques can achieve a very effective image of the soft tissues of the heart and vascular system. MRI procedures can also image these features without delivering a high dosage of radiation to the body of the patient, and, as a result, MRI procedures may be reliably and safely repeated. However, MRI devices may operate at frequencies of 10 megahertz or higher, which may cause energy to be transferred to the lead. In particular, the high frequency fields induce a voltage in the lead, causing the potential of the lead to be higher than the surrounding tissue. In effect, the lead behaves as an antenna. Current may flow from the electrode into the tissue proximate to the electrode due to induced voltage. It is therefore desirable to develop leads that reduce the amount of current that is conducted to the tissue proximate the electrode.

SUMMARY

This disclosure provides a medical lead assembly that includes a lead body having a proximal end configured to couple to an implantable medical device and a distal end. The lead assembly further includes an electrode assembly located at the distal end of the lead body, the electrode assembly including a tip electrode, a conductive electrode shaft that is electrically coupled to the tip electrode and a conductive sleeve head that is coupled to at least a portion of the conductive electrode shaft at high frequencies to redirect current induced in the lead by a high frequency signal from the tip electrode to the conductive sleeve.

In one example, the disclosure is directed to a medical electrical lead comprising a lead body having a proximal end configured to couple to an implantable medical device and a distal end and an electrode assembly located at the distal end of the lead body. The electrode assembly includes a tip electrode, a conductive electrode shaft that is electrically coupled to the tip electrode, and an energy dissipating structure that is non-conductively coupled to at least a portion of the conductive electrode shaft at high frequencies to redirect energy induced in the lead by a high frequency signal from the tip electrode to the energy dissipating structure.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

The present disclosure provides an electrode assembly for a medical lead that redirects a significant portion of the current induced by high frequency signals (e.g., greater than or equal to 1 MHz) away from an electrode of the lead that is in contact with a tissue of the patient, e.g., a tip electrode, without redirecting only a small portion of the current associated with low frequency signals (e.g., less than or equal to 1 kHz). Instead, the current induced by the high frequency signals are directed to and dissipated by an energy dissipating structure, such as a conductive sleeve head near the distal end of the lead. By redirecting the current induced by the high frequency signals away from the tip electrode, the tip electrode does not experience a surge in current density when exposed to high frequency signals, which, in turn, eliminates unintended heat being transferred from the tip electrode to the tissue around the tip electrode. Consequently, a patient with a medical electrical lead constructed in accordance with the techniques described in this disclosure may undergo an MRI procedure without significantly affecting the operation of the medical electrical lead.

Although described in the context of MRI procedures, the techniques of this disclosure may also allow the patient to undergo other medical procedures that utilize high frequency signals that may affect operation of the medical electrical lead, such as an electrocautery procedure, diathermy procedure, ablation procedure, electrical therapy procedure, magnetic therapy procedure, or the like. Moreover, the electrode assemblies described in this disclosure may also reduce the affect of high frequency signals encountered in non-medical environments, such in an environment with RF security gates.

Figure 1:
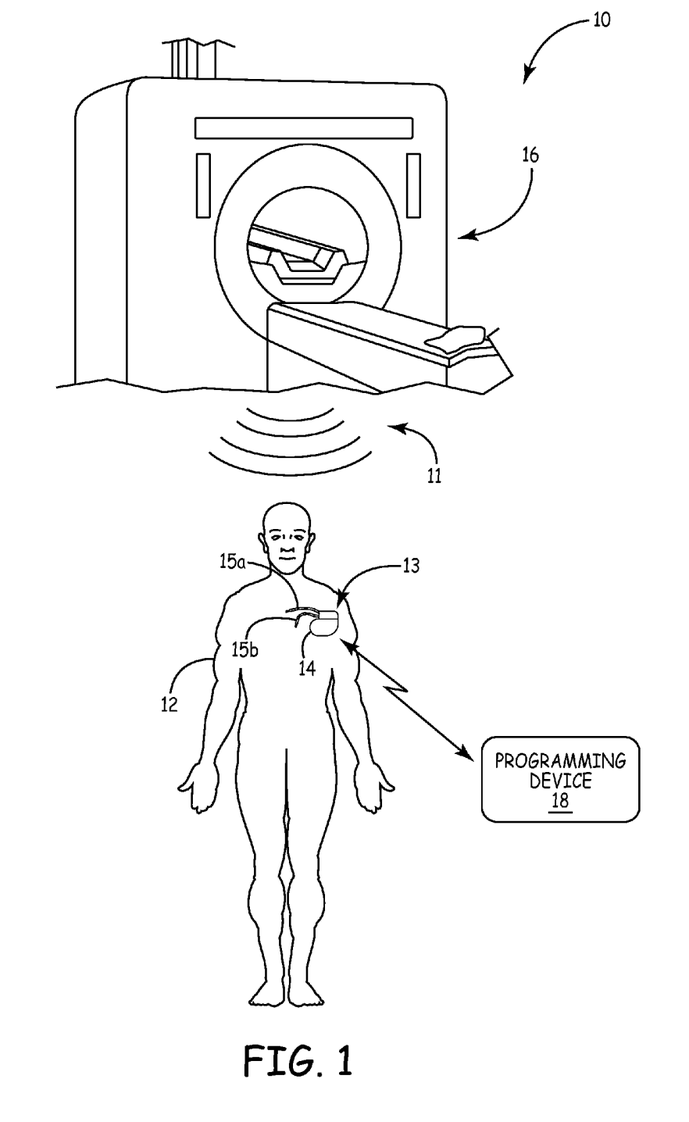
FIG. 1 is a conceptual diagram illustrating an environment in which a medical device system is exposed to a disruptive energy field.

FIG. 1 is a conceptual diagram illustrating an environment 10 in which a medical device system 13 is exposed to a disruptive energy field 11. System 13 includes an implantable medical device (IMD) 14 and one or more medical lead assemblies 15a,b that extend from the IMD 14 to a target location within patient 12. IMD 14 is implanted within patient 12 to provide therapy to and/or to monitor a physiological condition of patient 12. IMD 14 may be any of a variety of devices that provide therapy to patient 12, monitor a condition of patient 12, or both. For example, IMD 14 may be a device that provides electrical stimulation therapy via implantable lead assemblies 15a,b that include one or more electrodes. In some instances, IMD 14 may be a device that provides electrical stimulation therapy in the form of cardiac rhythm management therapy to a heart of patient 12 via leads implanted within one or more atria and/or ventricles of the heart. In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

Environment 10 includes an energy source that generates disruptive energy field 11 to which medical device system 13 is exposed. In the example illustrated in FIG. 1, the energy source or disruptive field source is an MRI scanner 16. Although the techniques of this disclosure are described with respect to disruptive energy field 11 generated by MRI scanner 16, medical device system 13 may be used within environments in which other types of disruptive energy fields, medical and non-medical, are present. For example, medical device system 13 may be used in environments in which disruptive energy field 11 is generated by other sources, such as an external cardioversion device, external defibrillator, electrocautery device, diathermy device, ablation device, radiation therapy device, electrical therapy device, magnetic therapy device, CT scanner, X-ray machine, RFID security gate, or any other environment with devices that radiate energy to produce magnetic, electromagnetic, electric fields or other disruptive energy fields.

MRI scanner 16 uses magnetic and RF fields to produce images of body structures for diagnosing injuries, diseases and/or disorders. In particular, MRI scanner 16 may generate a static magnetic field, gradient magnetic fields and RF fields. The static magnetic field is a non-varying magnetic field that is typically always present around MRI scanner 16 whether or not an MRI scan is in progress. Gradient magnetic fields are pulsed magnetic fields that are typically only present while the MRI scan is in progress. RF fields are pulsed RF fields that are also typically only present while the MRI scan is in progress. The magnitude, frequency or other characteristic of disruptive energy field 11 may vary based on the type of MRI scanner producing the field or the type of MRI scan being performed.

Some or all of the various types of fields produced by MRI scanner 16 may interfere with operation of one or more components of medical device system 13, e.g., IMD 14 and/or medical lead assemblies 15a,b extending from IMD 14. In other words, one or more of the various types of fields produced by MRI scanner 16 may make up disruptive energy field 11. For example, the RF fields produced by MRI scanner 16 may induce energy on one or more of medical lead assemblies 15a,b coupled to IMD 14. The induced energy on lead assemblies 15a,b or on the components of the IMD may result in the tip electrode experiencing a surge in current density, which, in turn, may cause unintended heat being transferred from the tip electrode to the tissue around the tip electrode. Such heating may compromise pacing and sensing thresholds at the site, which could result in reduced therapy efficacy.

As will be described in detail below, one or more implantable lead assemblies 15a,b extending from IMD 14 include an electrode assembly that redirects energy (e.g., current) induced by the RF signals of MRI scanner 16 (or other high frequency signals in the cases in which the source is not an MRI scanner) away from a tip electrode of the lead. Instead, the energy induced by the high frequency signals is directed and dissipated via an energy dissipating structure (referred to herein as a conductive sleeve head) of lead assemblies 15a,b. By redirecting the energy induced by the high frequency signals away from the tip electrode, the tip electrode does not experience a surge in current density, which, in turn, reduces the amount of unintended heat being transferred from the tip electrode to the tissue around the tip electrode.

A user, such as a physician, technician, or other clinician, may interact with a programming device 18 to communicate with IMD 14. For example, the user may interact with programming device 18 to retrieve physiological information, diagnostic information, logs of delivered therapies, or an assessment of the performance or integrity of IMD 14, such as leads or a power source of IMD 14. For example, the user may use programming device 18 to retrieve information from IMD 14 regarding sensed physiological parameters of patient 12, such as electrical depolarization/repolarization signals from the heart (referred to as an "electrogram" or EGM), intracardiac or intravascular pressure, activity, posture, respiration or thoracic impedance.

The user may also interact with programming device 18 to program IMD 14, e.g., select values for operational parameters of IMD 14. For electrical stimulation therapies, for example, the user may interact with programming device 18 to program a therapy progression, select an electrode or combination of electrodes of leads of IMD 14 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes. The operating parameters may be parameters of a normal operating mode or an exposure operating mode.

The user may interact with programming device 18 to manually configure IMD 14 into or out of the exposure operating mode. The user may, for example, interact with programming device 18 to program IMD 14 into the exposure operating mode prior to patient 12 undergoing a medical procedure in which IMD 14 will be exposed to a disruptive energy field 11, e.g., before undergoing a MRI scan. The user may also reprogram IMD 14 from the exposure mode to a normal mode after the MRI scan is finished.

Programming device 18 may communicate with IMD 14 via wireless communication using any techniques known in the art. Examples of communication techniques may include, for example, magnetic telemetry, low frequency telemetry, RF telemetry, tissue conductance telemetry (in which the body is used as a conductor), or acoustic telemetry, but other techniques are also contemplated. In some instances, programming device 18 and IMD 14 may communicate in the 402-405 MHz frequency band in accordance with the Medical Implant Communications Service (MICS) frequency band regulation, in the 401-402 MHz or 405-406 MHz frequency bands in accordance with the Medical External Data Service (MEDS) band regulations, in the unlicensed industrial, scientific and medical (ISM) band, or other frequency band.

Programming device 18 may be a dedicated hardware device with dedicated software for programming of IMD 14. Alternatively, programming device 18 may be an off-the-shelf computing device running an application that enables programming device 18 to program IMD 14. In some examples, programming device 18 may be a handheld computing device or a computer workstation. Programming device 18 may, in some instances, include a programming head that may be placed proximate to the patient's body near the implant site of IMD 14 in order to improve the quality or security of communication between IMD 14 and programming device 18. Programming device 18 may include one or more processors, such as one or more microprocessors, digital signal processors (DSPs), application specific integrated circuits (ASICs), field-programmable gate arrays (FPGAs), programmable logic circuitry, or the like, that may perform various functions and operations, such as those described herein.

Figure 2:
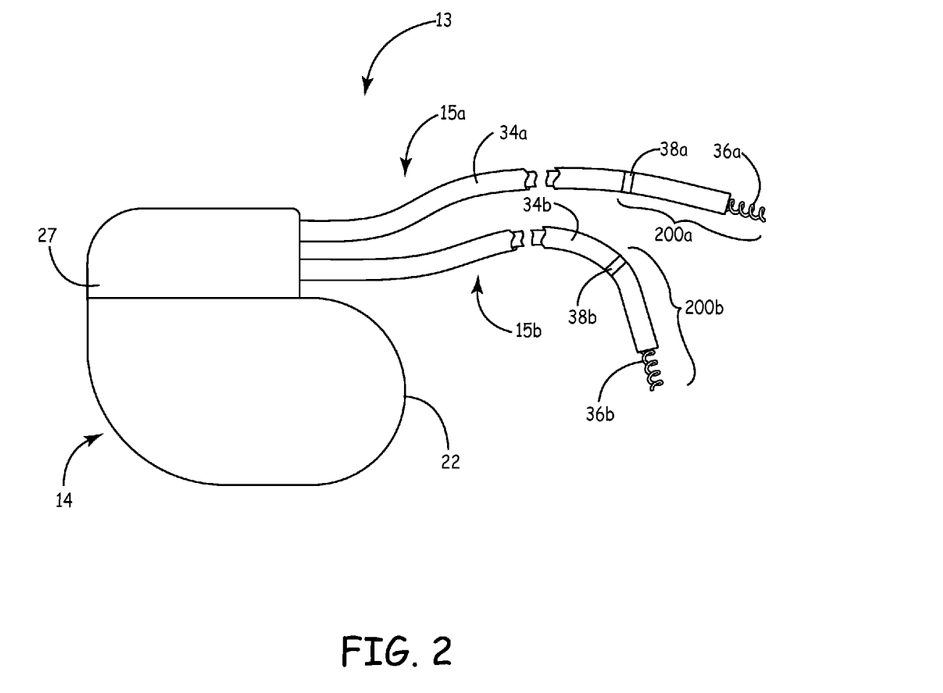
FIG. 2 is a conceptual perspective view of an example medical device system including an implantable medical device coupled to a lead according to an embodiment of the present disclosure.

FIG. 2 is a schematic diagram illustrating medical device system 13 of FIG. 1. Medical system 13 includes IMD 14 and lead assemblies 15*a, b*. IMD 14 may be an implantable cardiac device that senses electrical activity of a heart of patient 12 and/or provides electrical stimulation therapy to the heart of patient 12. The electrical stimulation therapy to the heart, sometimes referred to as cardiac rhythm management therapy, may include pacing, cardioversion, defibrillation and/or cardiac resynchronization therapy (CRT). The combinations of cardiac therapies provided may be dependent on a condition of patient 12. As such, IMD 14 may be an implantable pacemaker, implantable cardioverter defibrillator (ICD), cardiac resynchronization therapy defibrillator device, or other cardiac therapy device. In other instances, IMD 14 may be an implantable monitoring device, such as a loop recorder.

The IMD 14 includes a hermetically sealed housing 22. Housing 22 can be made of a substantially inert material or of a conducting material. IMD 20 may also include a connector body 27 that extends from or is integrated with the housing 22. Connector body 27 includes one or more ports that interconnect with connector terminals of respective ones of lead assemblies 15*a,b* at a proximal end of lead assemblies 15*a,b*.

The lead assemblies 15*a,b* generally include respective lead bodies 34*a,b* each having respective electrode assemblies 200*a,b* located near a distal end of lead assemblies 15*a,b*. As will be described in further detail herein, electrode assemblies 200*a,b* each include one or more electrodes and an energy dissipating structure. In the example illustrated in FIG. 2, electrode assemblies 200*a,b* each include a respective ring electrode 38*a,b* and tip electrode 36*a,b*. However, either or both of electrode assemblies 200*a,b* may include more than two electrodes or only a single electrode. For example, either or both of electrode assemblies 200*a,b* may include a plurality of ring electrodes along lead bodies 34*a,b* without helical tip electrode 36*a,b* electrode. As another example, either or both of electrode assemblies 200*a,b* may include only tip electrode 36*a,b* and no ring electrodes. Additionally tip electrodes 36*a,b* may not be used for fixation, such as is the case with hemispherical electrodes or ring electrodes.

Electrode assemblies 200*a,b* may also include a fixation mechanism to affix the lead assemblies 15*a,b* to or in a selected tissue, muscle, nerve or other location within patient 12. The fixation mechanism may thus be used to position the electrodes of electrode assemblies 200*a,b* relative to the selected location of patient 12. The fixation mechanism may, in some instances, define a portion of the tip electrodes 36*a,b*. For example, tip electrodes 36*a,b* may take the form of extendable helically shaped electrode to facilitate fixation of the distal end of electrode assemblies 200*a,b* to patient 12. In other instances, however, one or both of tip electrodes 36*a,b* may take other forms and may be affixed to patient 12 using separate attachment mechanisms. Fixation mechanisms can be any appropriate type, including tines, a grapple mechanism, a helical or screw mechanism, a drug-coated connection mechanism in which the drug(s) serves to reduce infection and/or swelling of the tissue, or other attachment mechanism. In other instances, the fixation mechanism may be separate from tip electrode 36*a,b*.

Each of tip electrodes 36*a,b* and ring electrodes 38*a,b* is electrically coupled to a respective conductor within its associated lead bodies 34*a,b* 34 and 36. For example, a first electrical conductor can extend along the length of lead body 34*a* from connector body 27 and electrically couple to tip electrode 36*a* and a second electrical conductor can extend along the length of lead body 34*a* from connector body 27 and electrically couple to ring electrode 37*a*. The respective conductors may couple to circuitry, such as a therapy module or a sensing module, of IMD 14 via connections in connector body 27. The electrical conductors transmit therapy from the therapy module within IMD 14 to one or both of the electrodes and transmit sensed electrical signals form the electrodes to the sensing module within IMD 14.

When IMD 14 is capable of delivering electrical stimulation therapy, IMD 14 delivers the therapy (e.g., pacing pulses) to patient 12 via any combination of electrodes to cause depolarization of cardiac tissue of the heart of patient 12. For example, IMD 14 may deliver bipolar pacing pulses to patient 12 via electrodes 36*a* and 38*a* and/or electrodes 36*b* and 38*b*. In another example, IMD 14 may deliver unipolar pacing pulses to using a housing electrode (not shown) in conjunction with one of electrodes 36*a* and/or 36*b*. The housing electrode may be formed integrally with an outer surface of the housing 22 of IMD 14 or otherwise coupled to the housing. In some examples, the housing electrode is defined by an uninsulated portion of an outward facing portion of housing 22.

Electrodes 36*a,b* and/or 38*a,b* may also sense electrical signals attendant to the depolarization and repolarization of the heart of patient 12 and the sensed electrical signals are sensed by conducted to IMD 14 via one or more conductors of respective lead assemblies 15*a,b*. IMD 14 may use any combinations of the electrodes and/or the housing electrode for unipolar or bipolar sensing. As such, the configurations of electrodes used by IMD 14 for sensing and pacing may be unipolar or bipolar depending on the application. IMD 14 may analyze the sensed signals to monitor a rhythm of the heart of patient 12 to detect an arrhythmia of the heart, e.g., tachycardia, bradycardia, fibrillation or the like. In some instances, IMD 14 provides pacing pulses (or other therapy)

to the heart based on the cardiac signals sensed within the heart. In other words, pacing may be responsive to the sensed events.

IMD 14 and lead assemblies 15*a,b* can be implanted in patient 12. The number and position of lead assemblies 15*a,b* can depend upon the type of IMD and the malady of the patient 12. For example, the leads can be positioned transvenously to positions within the heart or on the outside of the heart. The IMD 14 can be provided to pace the heart, defibrillate the heart, cardiovert the heart, resynchronize the heart and/or sense conditions of the heart via electrodes on lead assemblies 15*a,b* extending from IMD 14. Tip electrodes 36*a,b* and ring electrodes 38*a,b* can be positioned at various positions in the heart of patient 14, such as in one or more the ventricles or atria thereof.

The configuration of medical system 13 illustrated in FIG. 2 is merely an example. In other examples, medical system 13 may include more or fewer leads extending from IMD 14. For example, IMD 14 may be coupled to three leads, e.g., a third lead implanted within a left ventricle of the heart. In another example, IMD 14 may be coupled to a single lead that is implanted within either an atrium or ventricle of the heart. As such, IMD 14 may be used for single chamber or multi-chamber cardiac rhythm management therapy.

In addition to more or fewer leads, each of the leads may include more or fewer electrodes. In instances in which IMD 14 is used for therapy other than pacing, e.g., defibrillation or cardioversion, the leads may include elongated electrodes, which may, in some instances, take the form of a coil. IMD 14 may deliver defibrillation or cardioversion shocks to the heart via any combination of the elongated electrodes and housing electrode. As another example, medical system 13 may include leads with a plurality of ring electrodes, e.g., as used in some implantable neurostimulators.

In still other examples, medical system 13 may include epicardial leads and/or patch electrodes instead of or in addition to the transvenous lead assemblies 15*a,b* illustrated in FIG. 2. Further, IMD 14 need not be implanted within patient 12. In examples in which IMD 14 is not implanted in patient 12, IMD 14 may deliver electrical stimulation therapy to the heart via percutaneous leads that extend through the skin of patient 12 to a variety of positions within or outside of the heart.

The techniques of this disclosure are described in the context of cardiac rhythm management therapy for purposes of illustration. The techniques of this disclosure, however, may be used in IMDs that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 3:
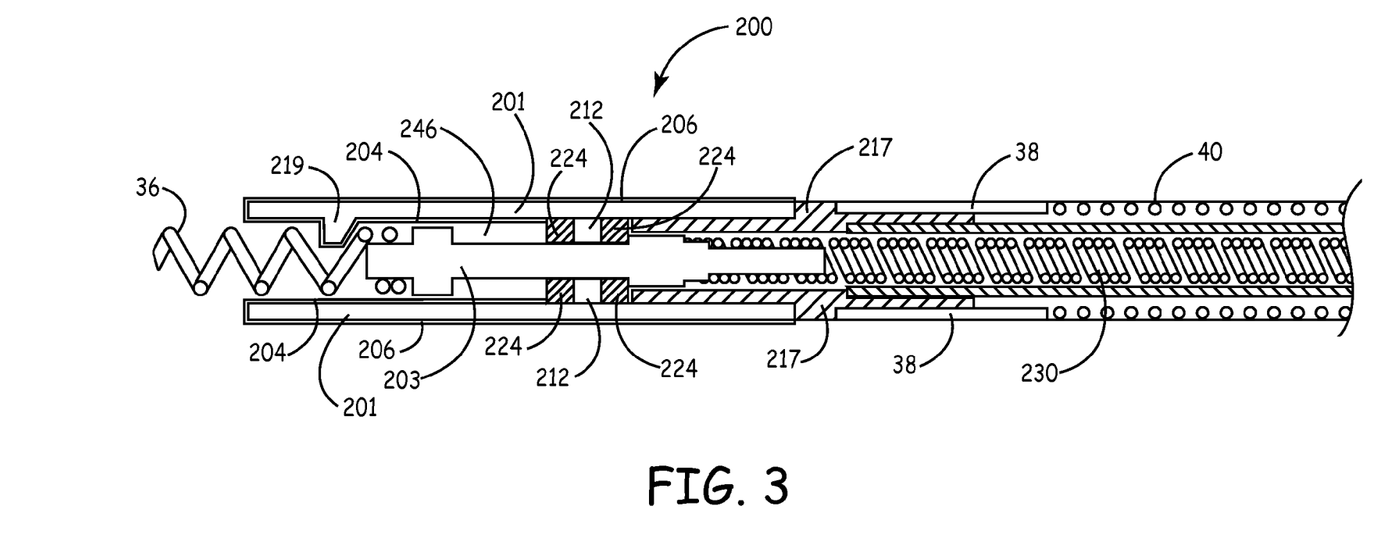
FIG. 3 is a longitudinal cross-sectional view of an example electrode assembly located at a distal end of a medical lead.

FIG. 3 is a schematic diagram illustrating an example electrode assembly 200 in further detail. Electrode assembly 200 may correspond with electrode assembly 200*a* of lead assembly 15*a* or electrode assembly 200*b* of lead assembly 15*b* of FIG. 2. Electrode assembly 200 includes a tip electrode 36 and a ring electrode 38 separated by a non-conductive spacer 217. As described above, however, electrode assembly 200 may include more than two electrodes or only a single electrode (e.g., only tip electrode 36).

Lead assembly 15 includes a tip conductor 230 that extends along a length of the lead and electrically couples to a conductive electrode shaft 203. Tip conductor 230 and electrode shaft 203 may be mechanically coupled in addition to being electrically coupled. Tip electrode 36 is electrically and, in some instances, mechanically coupled to the opposite end of electrode shaft 203. The mechanical coupling may be achieved via spot welding, clinching or other suitable mechanism. Conductive electrode shaft 203 and/or tip electrode 36 may be made from any conductive material, including platinum, platinum iridium, tantalum, titanium, titanium alloy, conductive polymers, and/or other suitably conductive material. Tip conductor 230 may, in some instances, be separate pieces or multiple components that are interconnected (e.g., a multifilar wire). The electrical conductors can also be coated and non-coated cables.

Tip electrode 36 may be retractable such that it may be controlled to extend from and retract within the distal end of electrode assembly 200. During implantation, a user may interact with lead assembly 15 to rotate tip conductor 230, which causes electrode shaft 203 to rotate and extend tip electrode 36 from the distal end of electrode assembly 200. In this manner, tip electrode 36 may be screwed into the target tissue location within patient 12. As such, tip conductor 230 may have sufficient rigidity to assist in attaching electrode assembly 200 to the target tissue location while being flexible to navigate through a body lumen of patient 12, e.g., through one or more veins. In other instances, electrode shaft 203 may be formed to receive a stylet to allow a user to rotate electrode shaft 203 to extend and/or retract tip electrode 36.

Lead assembly 15 also includes a ring conductor 40 that extends along a length of the lead and electrically couples to ring electrode 38. Ring conductor 40 and ring electrode 38 may be mechanically coupled (e.g., via spot welding, clinching or other mechanism) in addition to being electrically coupled. Ring electrode 38 may have a cylindrical shape, but other shaped electrodes may be utilized in place of a ring electrode. Ring conductor 40 is illustrated in FIG. 3 as having a larger diameter than tip conductor 230. In other instances, tip conductor 230 may have a larger diameter than ring conductor 40 or may have an equal diameter and run the length of the catheter body intertwined with one another.

At the proximal end of electrode assembly 200, tip conductor 230 and ring conductor 40 are electrically coupled to circuitry of IMD 14, such as an electrical stimulation module or sensing module. Electrical stimulation may be delivered from IMD 14 to and sensed electrical signals may be delivered from tip electrode 36 and/or ring electrode 38 via their respective conductors.

Exposure of lead assembly 15 to an MRI device 16 or other therapeutic or diagnostic device that generates high frequency signals may cause certain undesirable effects. In the case of an MRI scan, lead assembly 15 may be subject to strong gradient magnetic fields and high frequency radio frequency (RF) pulses (e.g., about 42 mega hertz (MHz) per tesla), which can induce energy (e.g., in the form of currents) within lead assembly 15. The current induced in lead assembly 15 can cause certain undesirable effects, including heating, of the various lead components. Because of the small surface area of tip electrode 36, heating at tip electrode 36 is particularly undesirable.

According to various embodiments, such as those discussed herein, components or mechanisms can be provided to reduce or eliminate the amount of current conducted to tip electrode 36. As illustrated in FIG. 3, electrode assembly 200 includes a conductive sleeve head 201 to which at least a portion of the current induced by the high frequency RF pulses or gradient magnetic fields of MRI device 16 may be redirected. Redirecting or shunting at least a portion of the induced current to conductive sleeve head 201 increases the area over which the current or thermal energy is dissipated, thereby decreasing the amount of heating. Conductive sleeve head 201 may be made from any conductive material, including titanium, titanium alloy, conductive polymers, tantalum, platinum, platinum iridium and/or other suitably conductive material. Although described in the context of conductive sleeve head 201, the energy dissipating structure of lead assembly 15 may be part of a housing, a ring electrode, a sheath, or other structure of lead assembly 15.

Conductive sleeve head 201 may, in one example, comprise a cylindrical shape (e.g., a ring shape). In other instances, however, conductive sleeve head 201 may take on any of a variety of other shapes. Conductive sleeve head 201 may surround at least a portion of conductive electrode shaft 203. Conductive sleeve head 201 may also surround a portion of tip electrode 36 and/or tip conductor 230. An inner diameter of most of conductive sleeve head 201 is larger than an outer diameter of tip electrode 36 and electrode shaft 203 to form a space 246. However, in other instances as in the case of a passive lead, tip electrode 36 may have a diameter that is at least as large as conductive sleeve head 201. Conductive sleeve head 201 may have an outer diameter of between approximately 1.3 and 2.8 mm, an inner diameter of between approximately 1 and 2 mm, and a length between approximately 3 and 10 mm. The surface area of conductive sleeve head 201 may be between approximately 20-100 mm$^2$ which is much larger than the surface area of tip electrode 36, which is approximately 5.5 mm$^2$. A large surface area ratio, defined by the ratio of the surface area of conductive sleeve head 201 to the surface area of tip electrode 36, is desired to spread the current induced from MRI device 16 over a large area of electrode assembly 200. A tenfold (i.e., 10×) larger surface area ratio may result in about tenfold lower temperatures at tip electrode 36. However, conductive sleeve head 201 may have other dimensions giving it a larger or smaller surface area.

Conductive sleeve head 201 may further be shaped to form a protrusion 219 that extends from the inner diameter of conductive sleeve head 201 into the electrode assembly 200. Protrusion 219 may be configured such that it physically contacts a portion of electrode shaft 203 and/or tip electrode 36 to guide, stop or provide other mechanical function. Protrusion 219 may be formed of a non-conductive material. Alternatively, protrusion 219 may be formed from the same conductive material as the rest of conductive sleeve head 201 and a coating of non-conductive material may be placed on either conductive sleeve head 201 or at least a portion of electrode shaft 203. In this manner, there is no direct contact between the conductive material of conductive sleeve head 201 and the conductive material of tip electrode 36 or electrode shaft 203. In other words, conductive sleeve head 201 and conductive electrode shaft 203 are not conductively coupled to one another, e.g., via direct metal to metal contact. Eliminating or reducing the amount of contact between conductive material of conductive sleeve head 201 and the conductive material of tip electrode 36 or electrode shaft 203 reduces noise that may be produced by intermittent contact between the conductive materials. The noise from the intermittent contact may, in some instances, cause voltage peaks that may result in oversensing and inadvertent delivery or withholding of therapy. Additionally, the intermittent contact may result in corrosion of one or both of the conductive elements.

The current induced on tip electrode 36, electrode shaft 203 and tip conductor 230 by a high frequency signal may be at least partially coupled to conductive sleeve head 201. In one example, at least a portion of the current induced on tip electrode 36, electrode shaft 203 and tip conductor 230 may be coupled to conductive sleeve head 201 through a fluid within space 246. Space 246 may be filled with a bodily fluid (e.g., blood) when implanted within patient 12. Space 246 may alternatively be filled with a saline or other fluid prior to implantation. At least a portion of the current induced on tip electrode 36, electrode shaft 203 and tip conductor 230 by a high frequency signal may be redirected to conductive sleeve head 201 via a non-conductive coupling, e.g., capacitive coupling and/or thermal coupling. Redirecting at least a portion of the current to conductive sleeve head 201 reduces the amount of current delivered to the tissue adjacent to tip electrode 36 to reduce heating at the tip electrode to tissue interface. In other words, conductive sleeve head 201 increases the area over which the current induced on electrode shaft 203 and tip conductor 230 by high frequency signals is dissipated, thereby decreasing the amount of heating. In the case of low frequency signals, e.g., pacing pulses, defibrillation pulse or cardioversion shock, little or no current is redirected to conductive sleeve head 201.

In the case of capacitive coupling, electrode shaft 203 and conductive sleeve head 201 may be viewed as a capacitor with a portion of electrode shaft 203 being a first capacitive plate, a portion of conductive sleeve head 201 as a second capacitive plate, and the fluid or other material in space 246 being the dielectric between the two plates. At low frequencies and DC (e.g., during delivery of stimulation therapy), the capacitive coupling between electrode shaft 203 and conductive sleeve head 201 is small and not a lot of current is redirected to conductive sleeve head 201. However, at high frequencies (e.g., during an MRI scan) the capacitive coupling between electrode shaft 203 and conductive sleeve head 201 is high, resulting in a significant amount of the induced current or energy being redirected to conductive sleeve head 201. As such, conductive sleeve head 201 does not significantly interfere with delivery of therapy (e.g., pacing pulses).

In the case of thermal coupling, a temperature differential between electrode shaft 203, tip electrode 36 or conductor 230 and sleeve head 201 may thermally couple the energy to sleeve head 201.

In some instances, conductive sleeve head 201 may be at least partially covered by an insulating coating. In other instances, conductive sleeve head 201 may be directly exposed to bodily fluid and/or tissue. In instances in which conductive sleeve head 201 is at least partially covered by insulating coating 206, insulating coating 206 may be located on an outer surface of conductive sleeve head 201. Insulating coating 206 may affect the capacitance of conductive sleeve head 201 and reduce the effect of conductive sleeve head 201 on the tip electrode to tissue interface impedances. For example, as the thickness of insulating coating 206 increases, the capacitance associated with conductive sleeve head 201 decreases and the impedance of conductive sleeve head 201 increases. As a result the amount of current redirected to conductive sleeve head is reduced. This may, in some instances, result in less current associated with therapy delivered by IMD 14 being redirected to conductive sleeve head 201. As the thickness of insulating coating 206 decreases, the capacitance associated with conductive sleeve head 201 increases and the impedance of conductive sleeve head 201 decreases. As a result the amount of current redirected to conductive sleeve head is increased. This may, in some instances, result in more current associated with therapy delivered by IMD 14 being redirected to conductive sleeve head 201. As such, the thickness of insulating coating 206 may be adjusted as described by a therapy system designer to achieve a satisfactory tradeoff between capacitance and impedance.

Conductive sleeve head 201 may include an insulating coating 204 on an inner surface of conductive sleeve head 201. Insulating coating 204 on the inner surface may prevent the conductive material of conductive sleeve head 201 from making direct contact with the conductive material of tip electrode 36, electrode shaft 203 and/or tip conductor 230 from movement during the cardiac cycle. Insulating coating 204 may be threaded such that as electrode shaft 203 is rotated tip electrode 36 extends from and retracts within the distal end of electrode assembly 200.

Figure 4:
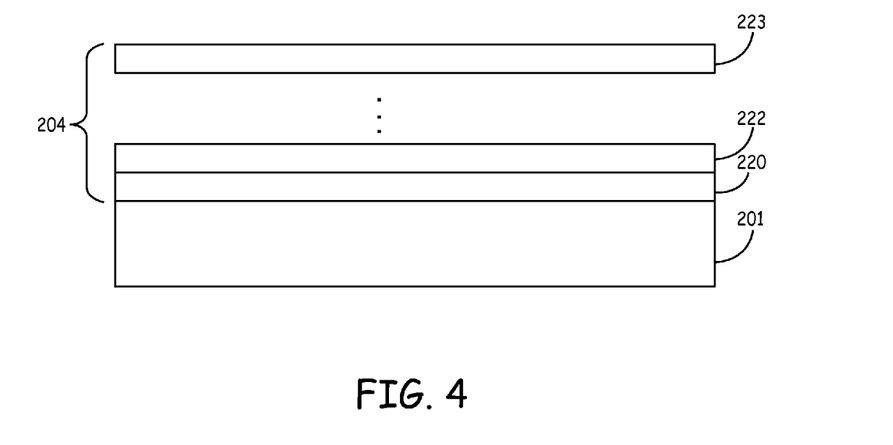
FIG. 4 depicts multiple layers of insulating material over a conductive element of an electrode assembly.
Figure 5A:
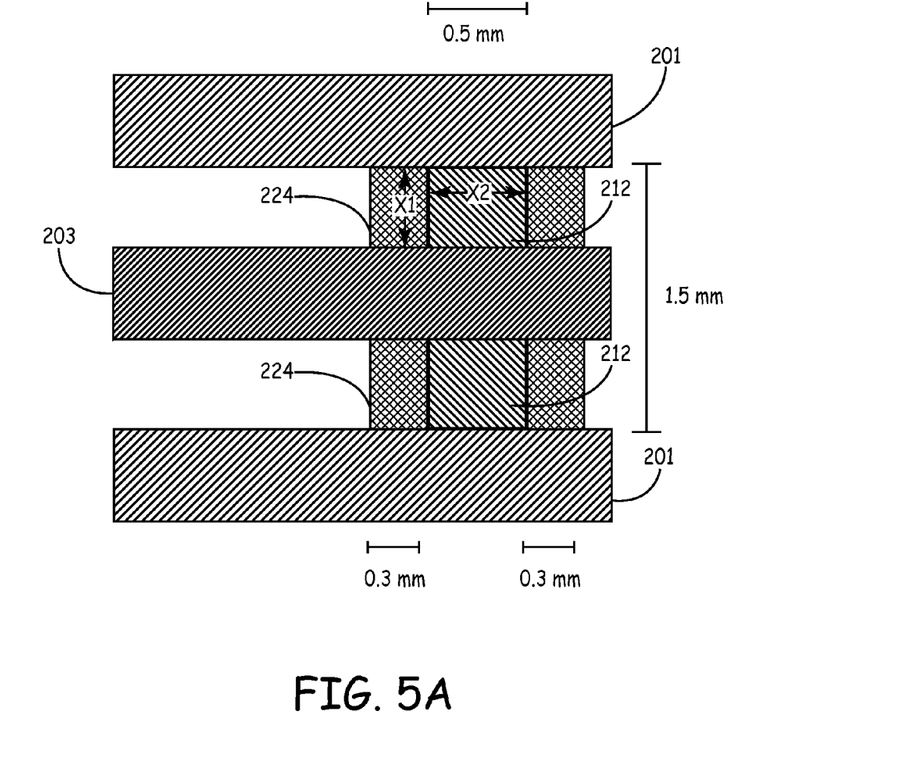
FIG. 5A depicts a cross-sectional view of a conductive ring coupled to a conductive seal for an electrode assembly.
Figure 5B:
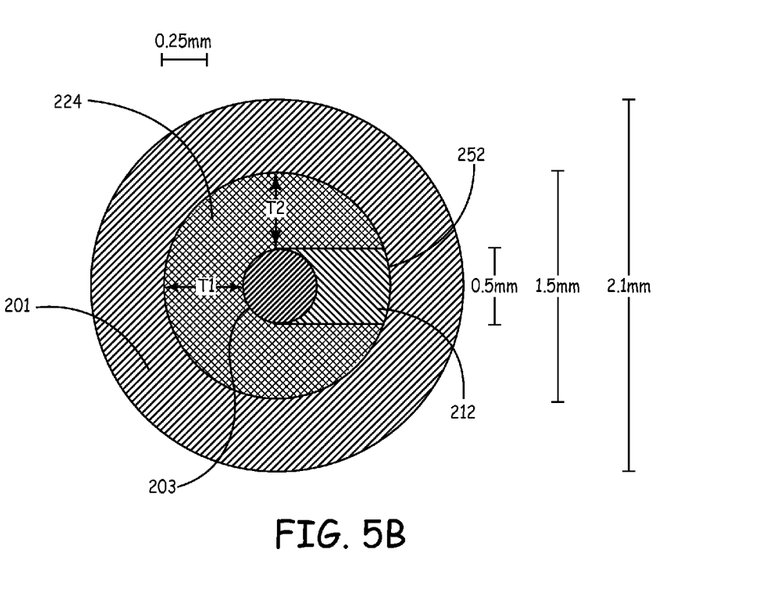
FIG. 5B depicts a top view of a conductive ring coupled to a conductive seal for an electrode assembly.
Figure 5C:
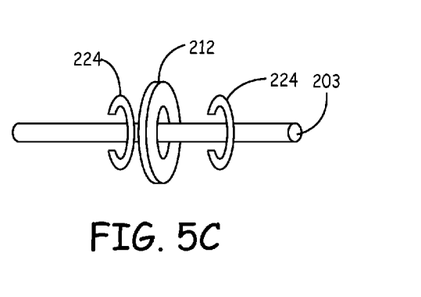
FIG. 5C depicts a cross-sectional view of conductive rings and a conductive seal coupled to a shaft of an electrode assembly.
Figure 5D:
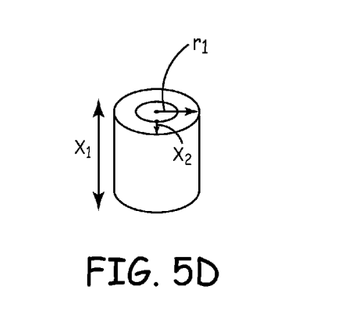
FIG. 5D depicts an angled view of a conductive seal of an electrode assembly.

Insulating coatings 204 and 206 may be formed of one or more layers of insulative material as described in further detail with respect to FIG. 4. FIG. 4 illustrates insulating coating 204 for purposes of example. Insulting coating 206 may be formed in a similar manner. In instances in which conductive sleeve head 201 includes both insulating coating 204 and 206, the coatings may be the same or different. Insulating coating 204 may be formed from a single layer of insulative material or multiple layers of insulative material. FIG. 4 illustrates insulating coating 204 being formed of multiple layers, including a first layer 220, second layer 222, and N layer 223, where N is a whole number. N will typically be less than 100, and more typically less than about 30 layers. Each layer may comprise different insulating materials, two or more different insulating materials, or the same insulating materials. The insulative materials forming each of layers 220, 222, 223 may be formed from any of a wide variety of insulating materials. Exemplary insulating materials include at least one or more of parylene, polyamide, metal oxides, polyimide, urethane, silicone, tetrafluroethylene (ETFE), polytetrafluroethylene (PTFE), or the like. Numerous techniques may be employed to introduce insulating material 204 over the outside of sleeve head 201 and/or partially inside sleeve head 201. Exemplary techniques include chemical vapor deposition, dip coating, thermal reflow, thermal extrusion, or other surface conversions.

Sleeve head 201 may be in contact with and, in some instances, mechanically coupled to, a seal 212 (also referred to as a sealing washer). Seal 212 is also in contact with electrode shaft 203. Seal 212 prevents fluid from passing through space 246 into the lumen defined by the lead body and housing tip conductor 230, ring conductor 40 and the like. Referring to FIGS. 5A-5D, seal 212 is substantially ring (i.e. o-ring) or disk shaped but other suitable shapes may also be employed. In one embodiment, seal 212 is defined by X1, X2 and radius (r1). X1 ranges from about 0.1 mm to about 0.50 mm, X2 extends from about 0.1 mm to about 1.0 mm, and r1 extends from about 0.5 mm to about 1.0 mm. Curved end 252 extends to about 1.25 mm from the center of shaft 203 and includes a curve defined by a radius of about 0.5 mm. These dimensions are provided for exemplary purposes only and should not be considered limiting. The dimensions of seal 212 will depend on the size and/or configuration of other components of lead assembly 15. Seal 212 may be formed from a non-conductive material or be formed from a conductive material with a non-conductive coating.

Electrode assembly 200 may also include one more rings, such as parallel rings 224 (e.g., C-rings) illustrated in FIGS. 3 and 5A-5D, that may hold or support seal 212 in place and/or act as markers. In other instances rings 224 may not provide any other function than coupling energy to conductive sleeve head 201 as described below. In some instances, sleeve head 201 and/or electrode shaft 203 may also be in contact with one or more rings. Rings 224 of FIGS. 3 and 5A-5D are shaped as a C-ring to receive seal 212. However, rings of other shapes may be used. Rings 224 have an outer diameter of about 1.5 mm, an inner diameter of about 0.7 mm, and a thickness that ranges from about 0.25 mm (T1) to about 0.5 mm (T2).

Seal 212 and rings 224 may, in some instances, be comprised a conductive material with a non-conductive coating. In this case, sleeve head 201 may capacitively or thermally couple to conductive electrode shaft 203 through seal 212 and/or rings 224 in addition to or instead of through fluid within space 246. In other words, seal 212 and/or rings 224 may reduce the distance over which energy is coupled to conductive sleeve head 201. For example, seal 212 and/or rings 224 may be coated with one of parylene, polyamide, metal oxides, polyimide, urethane, silicone, tetrafluroethylene (ETFE), polytetrafluroethylene (PTFE), or the like. In other instances, seal 212 and rings 224 may be comprised entirely of a non-conductive material. When seal 212 and/or rings 224 couple energy from electrode shaft 203 to conductive sleeve head 201 the surface area and thickness of the insulating coating on seal 212 and/or rings 224 may be adjusted to achieve the desired capacitance, impedance and/or resistance for improved coupling.

Electrode assembly 200 of lead assembly 15 illustrated in FIG. 3 is just one example of the techniques described in this disclosure. Electrode assembly 200 of lead assembly 15 may be configured differently without departing from the scope of the disclosure. As another example, a distal end of tip conductor 230 may be formed to achieve electrode shaft 203. For example, a portion of tip conductor 230 may be formed to serve as the electrode shaft. In this case, a portion of the conductor 230 may be exposed (e.g., has no insulative coating). Also, a diameter of tip conductor 230 may also be adjusted to form the interaction with seal 212.

Figure 6:
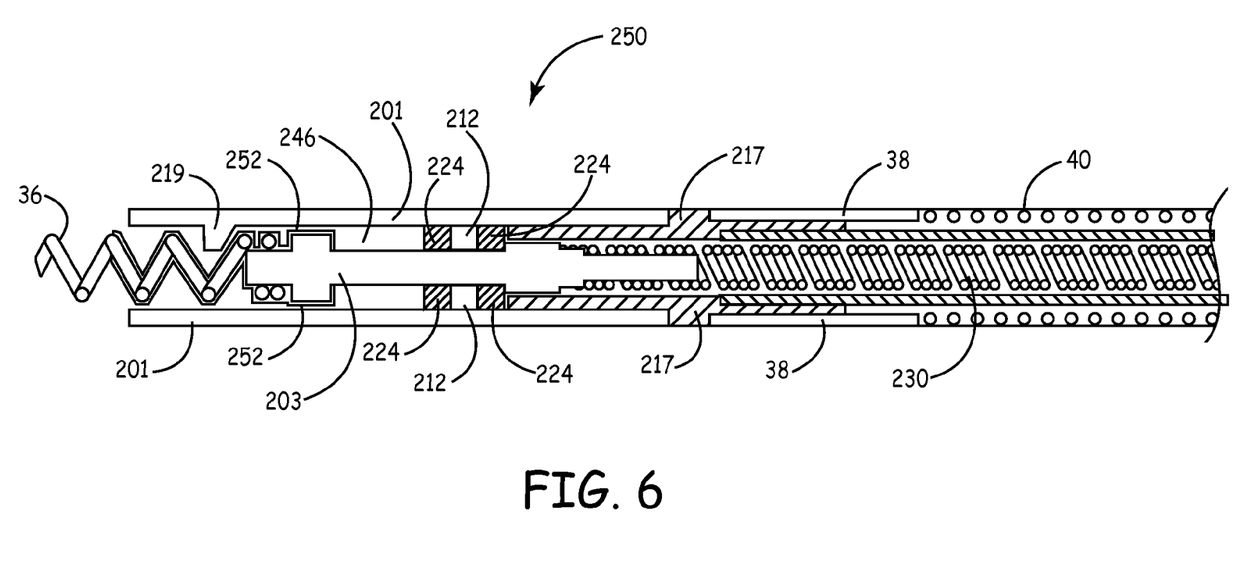
FIG. 6 is a longitudinal cross-sectional view of another example electrode assembly located at a distal end of a medical lead.

FIG. 6 is a schematic diagram illustrating another example electrode assembly 250 in further detail. Electrode assembly 250 of FIG. 6 conforms substantially with electrode assembly 200 of FIG. 3. However, electrode assembly 250 of FIG. 6 includes an insulative coating 252 on a portion of electrode shaft 203 instead of or in addition to insulative coating 204 on the inner surface of conductive sleeve head 201.

Figure 7:
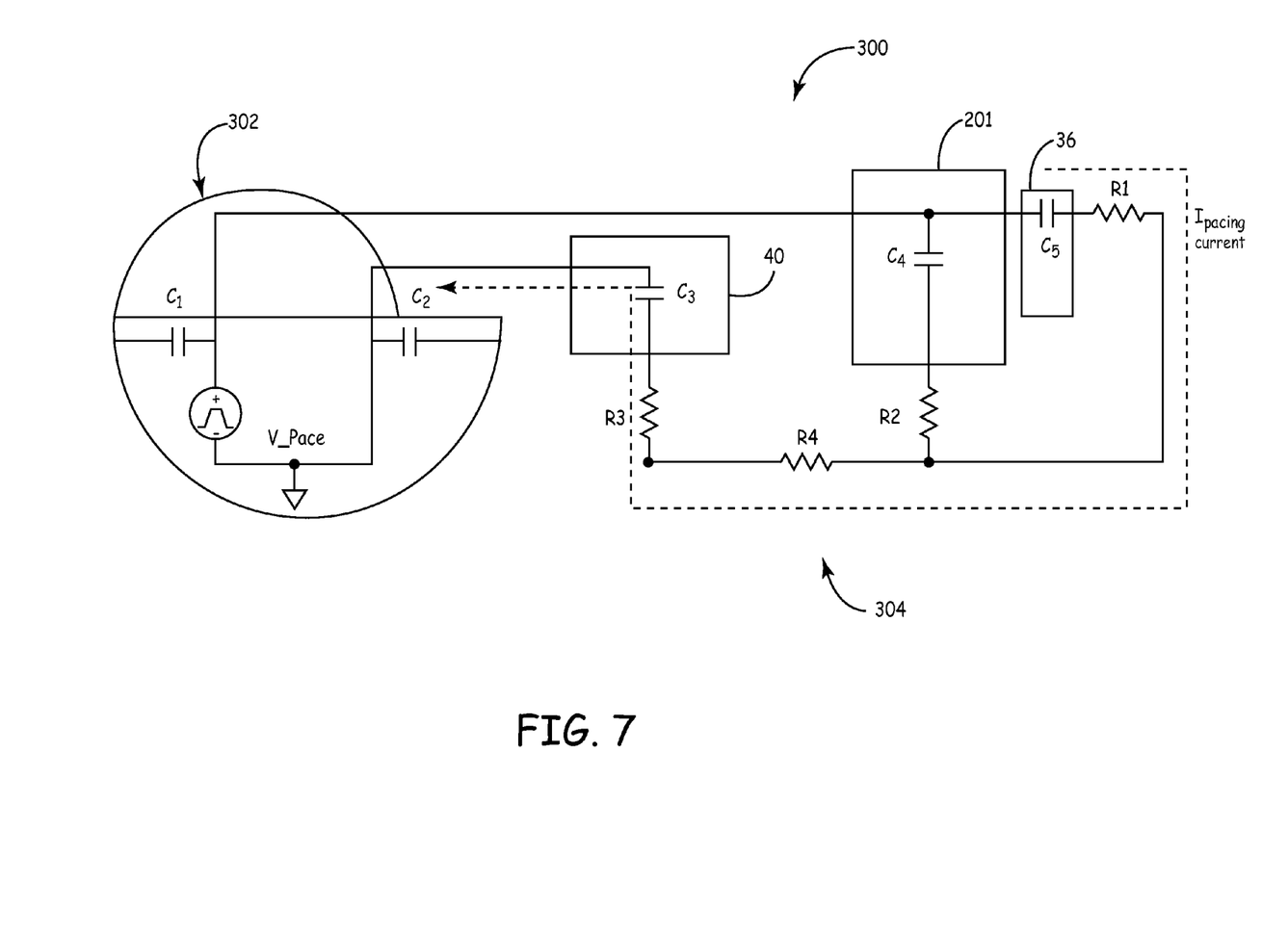
FIG. 7 is a circuit diagram illustrating an example circuit representing the medical system of FIGS. 1 and 2 during normal pacing conditions.

FIG. 7 is a circuit diagram illustrating an example circuit 300 representing system 13 during normal pacing conditions, e.g., when not exposed to disruptive energy field 11. Pacing conditions typically involve low frequency signals (e.g., less than 1 kHz). Circuit 300 includes an implantable medical device (IMD) circuit 302 (e.g. a pacemaker circuit, neurostimulator circuit, or the like) connected to a lead assembly circuit 304. IMD circuit 302 comprises two filter capacitors C1 and C2 connected to housing 102. C1 and C2 filter high frequency electromagnetic interference (EMI) so that high frequency signals do not affect the sensing operation of medical lead 106. An exemplary value for C1 is about 1 to 10 nanoFarad (nF) and C2 is 1-10 nF.

Lead assembly circuit 304 includes capacitors C3, C4, and C5, which correspond to electrical characteristics of ring electrode 38, sleeve head 201, and tip electrode 36, respectively. Resistors R1, R2, R3, and R4 represent the impedance created by tissue and/or blood of the patient. R1, R2, and R3 along with capacitors C5, C4, and C3 represent the tissue interface impedances. Generally, larger area electrodes result in larger values of capacitance and smaller values of resistance. However, the addition of insulating coating 206 over sleeve head 201 may reduce the effect of the tissue interface impedance and capacitance of conductive sleeve head 201. In particular, C4 comprises a series capacitance of the electrode to tissue interface and capacitance due to insulation. Exemplary values for lead assembly circuit 304 include C3 at approximately 10 microF (uF), R3 is approximately 100 Ohm (Ω), R2 is approximately 100Ω, C5 is approximately 1 uF, and R1 is approximately 500 Ω.

In one example, C4 is about 0.5 nanoFarad (nF) to about 10 nF and, more preferably between about 1-2 nF. In another example C4 may be between approximately 250 pF and 1 nF. For a sleeve head having a surface area of approximately 22 square millimeters (mm$^2$) and an insulating material 204 having a dielectric constant of approximately 4, for instance, a insulating layer thickness of approximately 68 micrometers provides an impedance of approximately 10 Ohms and a capacitance of approximately 250 pF, a thickness of approximately 34 micrometers provides an impedance of approximately 5 Ohms and a capacitance of approximately 500 pF, and a thickness of approximately 17 micrometers provides an impedance of approximately 2.5 Ohms and a capacitance of approximately 1 nF. These values are only exemplary in nature. The components of circuit 500 representing the electrical characteristics of electrode assembly 200 may be take on different values depending on the construction of electrode assembly 200, e.g., based on the surface area of tip electrode 36, the surface area of ring electrode 38, the surface area of sleeve head 201, the surface area of ring 224, the thickness of any insulating layers, the dielectric constant of the insulating layers, the material from which electrodes 36, 38 or sleeve head 201 are constructed of and the like.

Generally, under typical pacing conditions, pacing current ($I_{pacing\ current}$) flows from tip electrode 36 to ring electrode 38 and then returns to IMD circuit 302. Negligible or no current $I_{pacing\ current}$ passes through the RF shunted sleeve head 201 and resistor R2 because under a low frequency or direct current (DC) application, capacitor C4 acts like an open circuit to a constant voltage across its terminals. A majority of the $I_{pacing\ current}$ passes to the patient's tissue, represented as resistor R1, due to the large capacitance of C5 associated with tip electrode 36. The pacing pulse passes through the tissue and any bodily fluid and returns through ring electrode 38 represented as R3 and C3.

Figure 8:
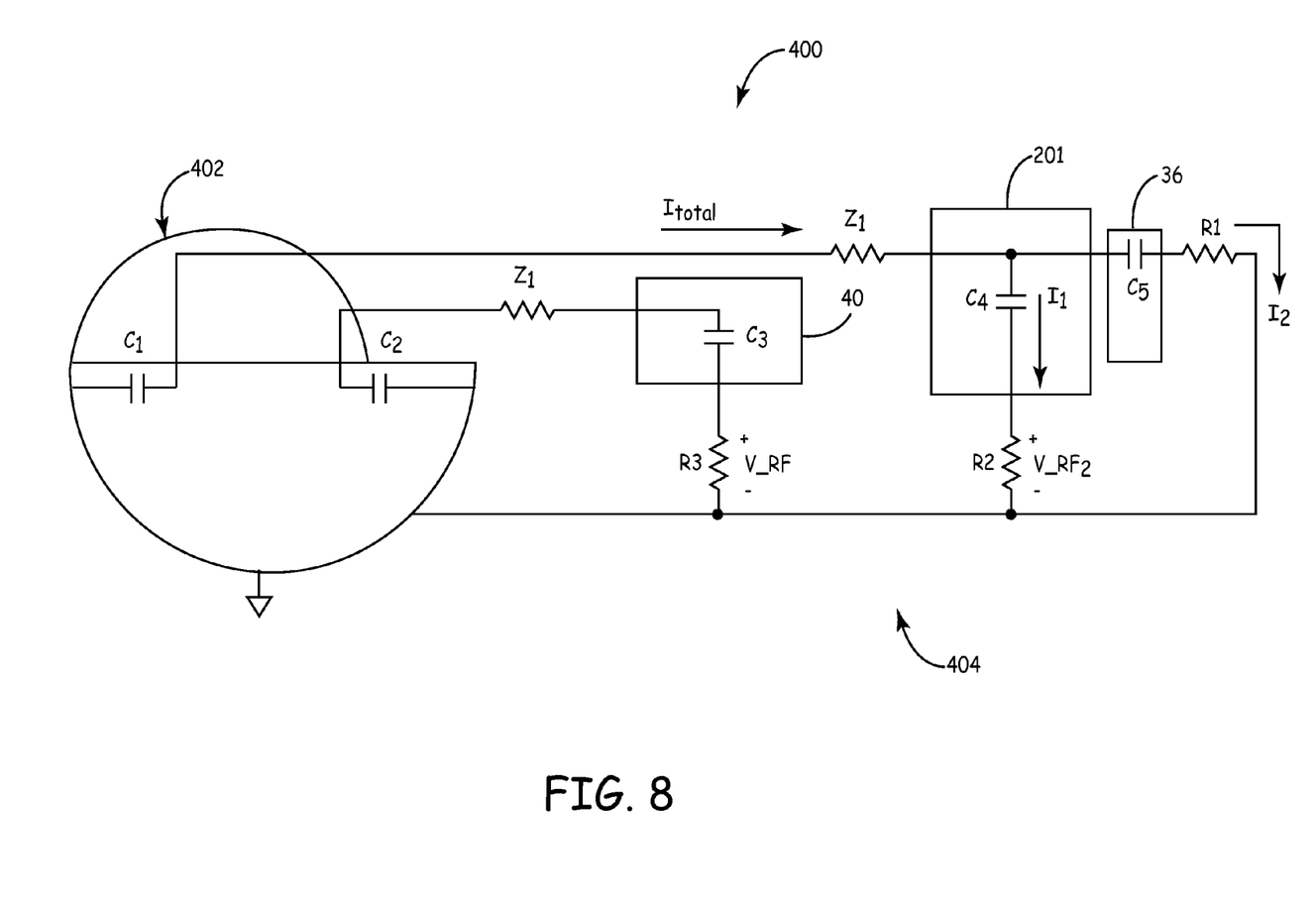
FIG. 8 is a circuit diagram illustrating an example circuit representing the medical system of FIGS. 1 and 2 during exposure to a disruptive energy field.

FIG. 8 is a circuit diagram illustrating a circuit 400 representing system 13 during exposure to disruptive energy field 11. Circuit 400 includes an IMD circuit 402 (e.g., a pacemaker circuit, neurostimulator circuit, or the like) and a lead assembly circuit 404. Circuit 400 includes the same elements as circuit 300, except lead resistance $Z_1$ is depicted between IMD circuit 402 and ring electrode 38 and also between IMD circuit 402 and conductive sleeve 201. Additionally, voltage potential differentiators (i.e. V_RF, V_RF2), are induced from disruptive field 11.

Under MRI conditions, a large current ($I_{total}$) is induced in the medical lead circuit 404 and IMD circuit 402 due to the RF voltage sources V_RF and V_RF2. A portion of the current, $I_1$, passes through the conductive sleeve head 201 represented by R2 and C4. Since the frequency of disruptive energy field 11 is large, the impedance associated with C4 is small resulting in a large portion of the total current flowing through conductive sleeve head 201. The remainder of the current, $I_2$, passes through tip electrode 36, represented by capacitor C5. The current then returns to capacitor C2 of IMD circuit 402 through ring electrode 38 and through the body tissue and housing 102. Because conductive sleeve head 201 has a large surface area relative to tip electrode 36, the total current is spread over a larger total surface area resulting in a lower current density. This results in reduced local heating at the tip of electrode 36. In sum, conductive sleeve head 201 and tip electrode 36 cooperate to serve as a high-pass filter, allowing only high frequencies signals to be redirected to conductive sleeve head 201 and low frequency signals are not redirected. Conductive sleeve head 201 serves as a capacitor and passes a large portion of the high frequency current (e.g., generated by an MRI or other high frequency source) into the blood stream surrounding conductive sleeve head 201 rather than through tip electrode 36 and into the myocardium tissue.

As described above with respect to FIGS. 7 and 8, conductive sleeve head 201 presents a high impedance at low frequencies. As such, at low frequencies (e.g., ~1 kHz for pacing signals), such as those used for pacing or other stimulation therapies, only a small amount of current is redirected to conductive sleeve head 201. In one example, less than approximately 5% of the current from low frequency pacing pulses are redirected to conductive sleeve head 201 and, in some instances, less than approximately 1%. However, the amount of current from low frequency signals that is redirected to conductive sleeve head 201 may be greater than or less than 5%, but still a small amount, e.g., less than 20% or, more preferably, less than 10%. At high frequencies, such as those produced during an MRI procedure, conductive sleeve head 201 presents a low impedance, resulting in a significant amount of the induced current being redirected to conductive sleeve head 201. In one example, at least approximately 80% of the current induced by the external field is redirected to conductive sleeve head 201, while less than approximately 20% of the induced current is conducted to tip electrode 36. However, the amount of current that is redirected away from tip electrode 36 may be smaller than or greater than 80%, e.g., approximately 50% or, more preferably, 60% or, even more preferably 70%. In this manner, the distal end of lead 24 is designed such that current from high frequency signals is redirected away from tip electrode 36 without significantly interfering with delivery of electrical stimulation therapy.

It is understood that the present disclosure is not limited for use in pacemakers, cardioverters of defibrillators. Other uses of the leads described herein may include uses in patient monitoring devices, or devices that integrate monitoring and stimulation features. In those cases, the leads may include sensors disposed on distal ends of the respective lead for sensing patient conditions.

The leads described herein may be used with a neurological device such as a deep-brain stimulation device or a spinal cord stimulation device. In those cases, the leads may be stereotactically probed into the brain to position electrodes for deep brain stimulation, or into the spine for spinal stimulation. In other applications, the leads described herein may provide muscular stimulation therapy, gastric system stimulation, nerve stimulation, lower colon stimulation, drug or beneficial agent dispensing, recording or monitoring, gene therapy, or the like. In short, the leads described herein may find useful applications in a wide variety of medical devices that implement leads and circuitry coupled to the leads.

Various examples have been described. These and other embodiments are within the scope of the following claims. For example, electrode 36a may include variously shaped electrodes such as ring shaped or other suitable shapes. Additionally, skilled artisans appreciate that other dimensions may be used for the mechanical and electrical elements described herein. It is also expected that the teachings herein, while described relative to a bipolar lead, can also be applied to a unipolar lead or other multipolar configurations as well as co-radial and multi-lumen configurations. These and other examples are within the scope of the following claims.

The invention claimed is:
1. A medical electrical lead comprising:
a lead body having a proximal end configured to couple to an implantable medical device and a distal end;

an electrical conductor passing from the proximal end through the lead body toward the distal end;

an electrode assembly located near the distal end of the lead body, the electrode assembly including:

a tip electrode;

a conductive electrode shaft that is electrically coupled to the tip electrode and is electrically coupled to the electrical conductor; and an energy dissipating structure that is coupled to the conductive electrode shaft via a non-electrically conductive material that provides a path to redirect energy induced in the lead by a high frequency signal from the tip electrode to the energy dissipating structure, wherein the electrode assembly further includes a coupling member that physically contacts the conductive electrode shaft and the energy dissipating structure with no metal-to-metal contact occurring between the coupling member and the conductive electrode shaft and wherein there is no electrically conductive path present between the conductive electrode shaft and the energy dissipating structure.

2. The medical electrical lead of claim 1, wherein the conductive electrode shaft includes a distal end that is electrically coupled to the tip electrode and a proximal end and wherein the electrical conductor is electrically coupled to the proximal end of the conductive electrode shaft.

3. The medical electrical lead of claim 1, wherein the coupling member is formed entirely of the non-electrically conductive material.

4. The medical electrical lead of claim 1, wherein the coupling member is formed of a conductive material with the non-electrically conductive material being a coating on the conductive material.

5. The medical electrical lead of claim 4, wherein the non-electrically conductive material comprises at least one of parylene, polyamide, metal oxide, polyimide, urethane, silicone, tetrafluroethylene (ETFE), and polytetrafluroethylene (PTFE).

6. The medical electrical lead of claim 4, wherein the coupling member includes at least one of a seal member and a ring member.

7. The medical electrical lead of claim 1, further comprising a dielectric coating that covers at least a portion of the energy dissipating structure.

8. The medical electrical lead of claim 7, wherein the dielectric coating covers at least an outer surface of the energy dissipating structure.

9. The medical electrical lead of claim 1, further comprising a dielectric material located between the energy dissipating structure and a portion of the electrode shaft that contacts the energy dissipating structure.

10. The medical electrical lead of claim 1, wherein the energy dissipating structure and the conductive electrode shaft are coupled to one another via a capacitive coupling or a thermal coupling.

11. The medical electrical lead of claim 1, wherein the electrode assembly further includes a ring electrode and the lead further includes a second conductor that extends from the proximal end of the lead body to the distal end of the lead body and is electrically coupled to the ring electrode.

12. The medical electrical lead of claim 1, wherein the high frequency signal comprises a high frequency signal of a magnetic resonance imaging (MRI) device.

* * * * *